United States Patent
Sinha et al.

(10) Patent No.: US 8,492,561 B2
(45) Date of Patent: Jul. 23, 2013

(54) AZETIDINE DERIVATIVES AS SPHINGOSINE 1-PHOSPHATE (S1P) RECEPTOR MODULATORS

(75) Inventors: Santosh C. Sinha, Ladera Ranch, CA (US); Smita S. Bhat, Irvine, CA (US); Evelyn G. Corpuz, Irvine, CA (US); Ken Chow, Newport Coast, CA (US); Wenkui K. Fang, Irvine, CA (US); Wha-Bin Im, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/305,701

(22) Filed: Nov. 28, 2011

(65) Prior Publication Data

US 2012/0142662 A1    Jun. 7, 2012

Related U.S. Application Data

(60) Provisional application No. 61/419,288, filed on Dec. 3, 2010.

(51) Int. Cl.
*A61K 31/397* (2006.01)
*C07D 205/04* (2006.01)

(52) U.S. Cl.
USPC ..................................... 548/950; 514/210.17

(58) Field of Classification Search
USPC ..................................... 548/950; 514/210.17
See application file for complete search history.

(56) References Cited

FOREIGN PATENT DOCUMENTS

WO    2010-093704    8/2010

OTHER PUBLICATIONS

Heinrich Stahl, 2002, Handbook of Pharmaceutical Salts, 329-345, Verlag Helvetica Chemica Acta—Zürich.
Jeffrey J. Hale, et al., Jan. 1, 2004, A Rational Utilization of High-Throughput Screeining Affords Selective, Orally Bioavailable 1-Benzyl-3-Carboxyazetidine, Journal of Medicinal Chemistry, 47 (27), 6662-6665.
L.C. Cross, 1976, Rules for the Nomenclature of Organic Chemistry, Section E: Stereochemistry, Pure & Appl. Chem., 45, 11-30.
Patent Cooperation Treaty, Notification of Transmittal of the International Search Report and the Written Opinion of the International Searching Authority, or the Declaration, Form PCT/ISA/220, Int. App. No. PCT/US2011/062241, Feb. 20, 2012.

*Primary Examiner* — Yong Chu
*Assistant Examiner* — Sonya Wright
(74) *Attorney, Agent, or Firm* — Doina G. Ene

(57) ABSTRACT

The present invention relates to novel azetidine derivatives, processes for preparing them, pharmaceutical compositions containing them and their use as pharmaceuticals as modulators of sphingosine-1-phosphate receptors.

11 Claims, No Drawings

AZETIDINE DERIVATIVES AS SPHINGOSINE 1-PHOSPHATE (S1P) RECEPTOR MODULATORS

CROSS REFERENCE TO RELATED APPLICATIONS

This application claims the benefit of U.S. Provisional Application Ser. No. 61/419,288 filed Dec. 3, 2010, which is hereby incorporated by reference in its entirety.

FIELD OF THE INVENTION

The present invention relates to novel azetidine derivatives, processes for preparing them, pharmaceutical compositions containing them and their use as pharmaceuticals, as modulators of sphingosine-1-phosphate receptors. The invention relates specifically to the use of these compounds and their pharmaceutical compositions to treat disorders associated with sphingosine-1-phosphate (S1P) receptor modulation.

BACKGROUND OF THE INVENTION

Sphingosine-1 phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular diseases. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

SUMMARY OF THE INVENTION

A group of novel azetidine derivatives, which are potent and selective sphingosine-1-phosphate modulators has been discovered. As such, the compounds described herein are useful in treating a wide variety of disorders associated with modulation of sphingosine-1-phosphate receptors. The term "modulator" as used herein, includes but is not limited to: receptor agonist, antagonist, inverse agonist, inverse antagonist, partial agonist, partial antagonist.

This invention describes compounds of Formula I, which have sphingosine-1-phosphate receptor biological activity. The compounds in accordance with the present invention are thus of use in medicine, for example in the treatment of humans with diseases and conditions that are alleviated by S1P modulation. In one aspect, the invention provides a compound having Formula I or a pharmaceutically acceptable salt thereof or stereoisomeric forms thereof, or the geometrical isomers, enantiomers, diastereoisomers, tautomers, zwitterions and pharmaceutically acceptable salts thereof

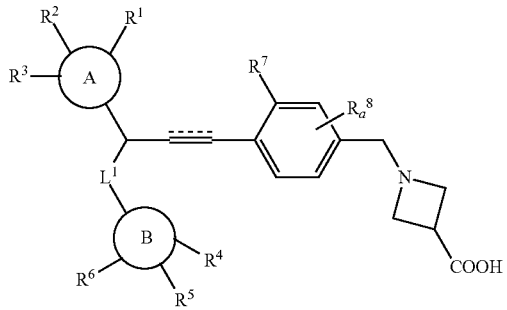

Formula I wherein:

"$\text{-----}$" represents a double bond "—$CR^{14}$=$CR^{15}$—" or a triple bond "—C≡C—";

A is $C_{6-10}$ aryl, heterocycle, $C_{3-8}$ cycloalkyl or $C_{3-8}$ cycloalkenyl;

B is $C_{6-10}$ aryl, heterocycle, $C_{3-8}$ cycloalkyl or $C_{3-8}$ cycloalkenyl;

$R^1$ is H, halogen, —$OC_{1-8}$ alkyl, $C_{1-8}$ alkyl, CN, C(O)$R^{11}$, $NR^{12}R^{13}$ or hydroxyl;

$R^2$ is H, halogen, —$OC_{1-8}$ alkyl, $C_{1-8}$ alkyl, CN, C(O)$R^{11}$, $NR^{12}R^{13}$ or hydroxyl;

$R^3$ is H, halogen, —$OC_{1-8}$ alkyl, $C_{1-8}$ alkyl, CN, C(O)$R^{11}$, $NR^{12}R^{13}$ or hydroxyl;

$R^4$ is H, halogen, —$OC_{1-8}$ alkyl, $C_{1-8}$ alkyl, CN, C(O)$R^{11}$, $NR^{12}R^{13}$ or hydroxyl;

$R^5$ is H, halogen, —$OC_{1-8}$ alkyl, $C_{1-8}$ alkyl, CN, C(O)$R^{11}$, $NR^{12}R^{13}$ or hydroxyl;

$R^6$ is H, halogen, —$OC_{1-8}$ alkyl, $C_{1-8}$ alkyl, CN, C(O)$R^{11}$, $NR^{12}R^{13}$ or hydroxyl;

$R^7$ is H, halogen, —$OC_{1-8}$ alkyl, $C_{1-8}$ alkyl, CN, C(O)$R^{11}$, $C_{6-10}$ aryl, heterocycle, $C_{3-8}$ cycloakyl, $C_{3-8}$ cycloalkenyl, $NR^{12}R^{13}$ or hydroxyl;

$R^8$ is the same or independently halogen, —$OC_{1-8}$ alkyl, $C_{1-8}$ alkyl, CN, C(O)$R^{11}$, $NR^{12}R^{13}$ or hydroxyl;

$L^1$ is O, S, NH or $CH_2$;

$R^{11}$ is H or $C_{1-8}$ alkyl;

a is 0, 1, 2 or 3;

$R^{12}$ is H or $C_{1-8}$ alkyl;

$R^{13}$ is H or $C_{1-8}$ alkyl;

$R^{14}$ is H or $C_{1-8}$ alkyl; and $R^{15}$ is H or $C_{1-8}$ alkyl.

In another aspect, the invention provides a compound having Formula I wherein

"$\text{-----}$" represents a double bond "—$CR^{14}$=$CR^{15}$—".

In another aspect, the invention provides a compound having Formula I wherein "$\text{-----}$" represents a triple bond "—C≡C—".

In another aspect, the invention provides a compound having Formula I wherein $L^1$ is $CH_2$.

In another aspect, the invention provides a compound having Formula I wherein $L^1$ is O, S or NH.

In another aspect, the invention provides a compound having Formula I wherein

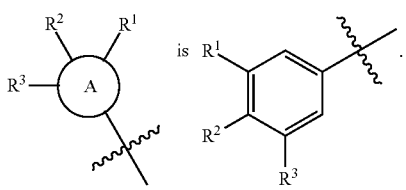

In another aspect, the invention provides a compound having Formula I wherein

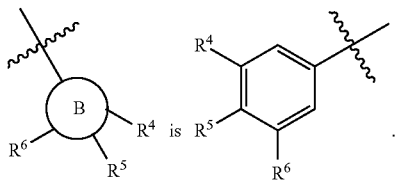

In another aspect, the invention provides a compound having Formula I wherein

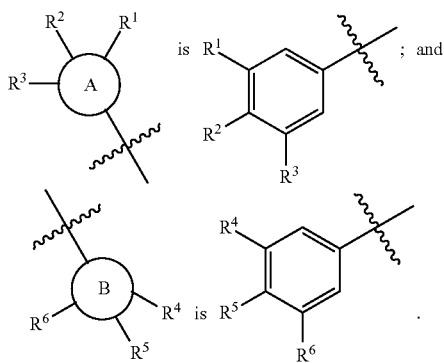

In another aspect, the invention provides a compound having Formula I wherein
"$=====$" represents a double bond "—$CR^{14}$=$CR^{15}$—";
A is $C_6$ aryl or heterocycle;
B is $C_6$ aryl or heterocycle;
$R^1$ is H, halogen, —$OC_{1-6}$ alkyl or $C_{1-6}$ alkyl;
$R^2$ is H, halogen, —$OC_{1-6}$ alkyl or $C_{1-6}$ alkyl;
$R^3$ is H, halogen, —$OC_{1-6}$ alkyl or $C_{1-6}$ alkyl;
$R^4$ is H, halogen, —$OC_{1-6}$ alkyl or $C_{1-6}$ alkyl;
$R^5$ is H, halogen, —$OC_{1-6}$ alkyl or $C_{1-6}$ alkyl;
$R^6$ is H, halogen, —$OC_{1-6}$ alkyl or $C_{1-6}$ alkyl;
$R^7$ is H, halogen, —$OC_{1-6}$ alkyl or $C_{1-6}$ alkyl;
$R^8$ is halogen, —$OC_{1-6}$ alkyl, $C_{1-6}$ alkyl, CN, $C(O)R^{11}$, $NR^{12}R^{13}$ or hydroxyl;
$L^1$ is O, S, NH or $CH_2$;
$R^{11}$ is H or $C_{1-3}$ alkyl;
a is 0 or 1;
$R^{12}$ is H or $C_{1-3}$ alkyl;
$R^{13}$ is H or $C_{1-3}$ alkyl;
$R^{14}$ is H or $C_{1-3}$ alkyl; and
$R^{15}$ is H or $C_{1-3}$ alkyl.

In another aspect, the invention provides a compound having Formula I wherein
"$=====$" represents a double bond "—$CR^{14}$=$CR^{15}$—";
A is $C_6$ aryl or heterocycle;
B is $C_6$ aryl or heterocycle;
$R^1$ is H, halogen, —$OC_{1-6}$ alkyl or $C_{1-6}$ alkyl;
$R^2$ is H, halogen, —$OC_{1-6}$ alkyl or $C_{1-6}$ alkyl;
$R^3$ is H, halogen, —$OC_{1-6}$ alkyl or $C_{1-6}$ alkyl;
$R^4$ is H, halogen, —$OC_{1-6}$ alkyl or $C_{1-6}$ alkyl;
$R^5$ is H, halogen, —$OC_{1-6}$ alkyl or $C_{1-6}$ alkyl;
$R^6$ is H, halogen, —$OC_{1-6}$ alkyl or $C_{1-6}$ alkyl;
$R^7$ is H, halogen, —$OC_{1-6}$ alkyl or $C_{1-6}$ alkyl;
$R^8$ is halogen, —$OC_{1-6}$ alkyl, $C_{1-6}$ alkyl, CN, $C(O)R^{11}$, $NR^{12}R^{13}$ or hydroxyl;
$L^1$ is $CH_2$;
$R^{11}$ is H or $C_{1-3}$ alkyl;
a is 0 or 1;
$R^{12}$ is H or $C_{1-3}$ alkyl;
$R^{13}$ is H or $C_{1-3}$ alkyl;
$R^{14}$ is H or $C_{1-3}$ alkyl; and
$R^{15}$ is H or $C_{1-3}$ alkyl.

In another aspect, the invention provides a compound having Formula I wherein
"$=====$" represents a double bond "—$CR^{14}$=$CR^{15}$—";
A is $C_6$ aryl or heterocycle;
B is $C_6$ aryl or heterocycle;
$R^1$ is H, halogen, —$OC_{1-6}$ alkyl or $C_{1-6}$ alkyl;
$R^2$ is H, halogen, —$OC_{1-6}$ alkyl or $C_{1-6}$ alkyl;
$R^3$ is H, halogen, —$OC_{1-6}$ alkyl or $C_{1-6}$ alkyl;
$R^4$ is H, halogen, —$OC_{1-6}$ alkyl or $C_{1-6}$ alkyl;
$R^5$ is H, halogen, —$OC_{1-6}$ alkyl or $C_{1-6}$ alkyl;
$R^6$ is H, halogen, —$OC_{1-6}$ alkyl or $C_{1-6}$ alkyl;
$R^7$ is H, halogen, —$OC_{1-6}$ alkyl or $C_{1-6}$ alkyl;
$R^8$ is halogen, —$OC_{1-6}$ alkyl, $C_{1-6}$ alkyl, CN, $C(O)R^{11}$, $NR^{12}R^{13}$ or hydroxyl;
$L^1$ is O, S or NH;
$R^{11}$ is H or $C_{1-3}$ alkyl;
a is 0 or 1;
$R^{12}$ is H or $C_{1-3}$ alkyl;
$R^{13}$ is H or $C_{1-3}$ alkyl;
$R^{14}$ is H or $C_{1-3}$ alkyl; and
$R^{15}$ is H or $C_{1-3}$ alkyl.

In another aspect, the invention provides a compound having Formula I wherein
"$=====$" represents a double bond "—$CR^{14}$=$CR^{15}$—";

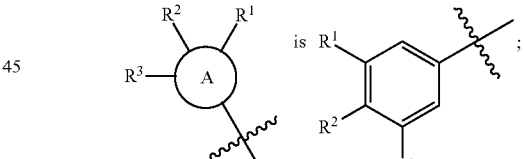

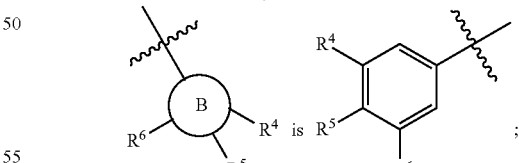

$R^1$ is H, halogen, —$OC_{1-6}$ alkyl or $C_{1-6}$ alkyl;
$R^2$ is H, halogen, —$OC_{1-6}$ alkyl or $C_{1-6}$ alkyl;
$R^3$ is H, halogen, —$OC_{1-6}$ alkyl or $C_{1-6}$ alkyl;
$R^4$ is H, halogen, —$OC_{1-6}$ alkyl or $C_{1-6}$ alkyl;
$R^5$ is H, halogen, —$OC_{1-6}$ alkyl or $C_{1-6}$ alkyl;
$R^6$ is H, halogen, —$OC_{1-6}$ alkyl or $C_{1-6}$ alkyl;
$R^7$ is H, halogen, —$OC_{1-6}$ alkyl or $C_{1-6}$ alkyl;
$R^8$ is halogen, —$OC_{1-6}$ alkyl, $C_{1-6}$ alkyl, CN, $C(O)R^{11}$, $NR^{12}R^{13}$ or hydroxyl;
$L^1$ is $CH_2$;

$R^{11}$ is H or $C_{1-3}$ alkyl;
a is 0 or 1;
$R^{12}$ is H or $C_{1-3}$ alkyl;
$R^{13}$ is H or $C_{1-3}$ alkyl;
$R^{14}$ is H or $C_{1-3}$ alkyl; and
$R^{15}$ is H or $C_{1-3}$ alkyl.

In another aspect, the invention provides a compound having Formula I wherein
" ===== " represents a triple bond "—C≡C—".
A is $C_6$ aryl or heterocycle;
B is $C_6$ aryl or heterocycle;
$R^1$ is H, halogen, —$OC_{1-6}$ alkyl or $C_{1-6}$ alkyl;
$R^2$ is H, halogen, —$OC_{1-6}$ alkyl or $C_{1-6}$ alkyl;
$R^3$ is H, halogen, —$OC_{1-6}$ alkyl or $C_{1-6}$ alkyl;
$R^4$ is H, halogen, —$OC_{1-6}$ alkyl or $C_{1-6}$ alkyl;
$R^5$ is H, halogen, —$OC_{1-6}$ alkyl or $C_{1-6}$ alkyl;
$R^6$ is H, halogen, —$OC_{1-6}$ alkyl or $C_{1-6}$ alkyl;
$R^7$ is H, halogen, —$OC_{1-6}$ alkyl or $C_{1-6}$ alkyl;
$R^8$ is halogen, —$OC_{1-6}$ alkyl, $C_{1-6}$ alkyl, CN, $C(O)R^{11}$, $NR^{12}R^{13}$ or hydroxyl;
$L^1$ is O, S, NH or $CH_2$;
$R^{11}$ is H or $C_{1-3}$ alkyl;
a is 0 or 1;
$R^{12}$ is H or $C_{1-3}$ alkyl; and
$R^{13}$ is H or $C_{1-3}$ alkyl.

In another aspect, the invention provides a compound having Formula I wherein
" ===== " represents a triple bond "—C≡C—".
A is $C_6$ aryl or heterocycle;
B is $C_6$ aryl or heterocycle;
$R^1$ is H, halogen, —$OC_{1-6}$ alkyl or $C_{1-6}$ alkyl;
$R^2$ is H, halogen, —$OC_{1-6}$ alkyl or $C_{1-6}$ alkyl;
$R^3$ is H, halogen, —$OC_{1-6}$ alkyl or $C_{1-6}$ alkyl;
$R^4$ is H, halogen, —$OC_{1-6}$ alkyl or $C_{1-6}$ alkyl;
$R^5$ is H, halogen, —$OC_{1-6}$ alkyl or $C_{1-6}$ alkyl;
$R^6$ is H, halogen, —$OC_{1-6}$ alkyl or $C_{1-6}$ alkyl;
$R^7$ is H, halogen, —$OC_{1-6}$ alkyl or $C_{1-6}$ alkyl;
$R^8$ is halogen, —$OC_{1-6}$ alkyl, $C_{1-6}$ alkyl, CN, $C(O)R^{11}$, $NR^{12}R^{13}$ or hydroxyl;
$L^1$ is O, S or NH;
$R^{11}$ is H or $C_{1-3}$ alkyl;
a is 0 or 1;
$R^{12}$ is H or $C_{1-3}$ alkyl; and
$R^{13}$ is H or $C_{1-3}$ alkyl.

In another aspect, the invention provides a compound having Formula I wherein
" ===== " represents a triple bond "—C≡C—".
A is $C_6$ aryl or heterocycle;
B is $C_6$ aryl or heterocycle;
$R^1$ is H, halogen, —$OC_{1-6}$ alkyl or $C_{1-6}$ alkyl;
$R^2$ is H, halogen, —$OC_{1-6}$ alkyl or $C_{1-6}$ alkyl;
$R^3$ is H, halogen, —$OC_{1-6}$ alkyl or $C_{1-6}$ alkyl;
$R^4$ is H, halogen, —$OC_{1-6}$ alkyl or $C_{1-6}$ alkyl;
$R^5$ is H, halogen, —$OC_{1-6}$ alkyl or $C_{1-6}$ alkyl;
$R^6$ is H, halogen, —$OC_{1-6}$ alkyl or $C_{1-6}$ alkyl;
$R^7$ is H, halogen, —$OC_{1-6}$ alkyl or $C_{1-6}$ alkyl;
$R^8$ is halogen, —$OC_{1-6}$ alkyl, $C_{1-6}$ alkyl, CN, $C(O)R^{11}$, $NR^{12}R^{13}$ or hydroxyl;
$L^1$ is $CH_2$;
$R^{11}$ is H or $C_{1-3}$ alkyl;
a is 0 or 1;
$R^{12}$ is H or $C_{1-3}$ alkyl; and
$R^{13}$ is H or $C_{1-3}$ alkyl.

In another aspect, the invention provides a compound having Formula I wherein
" ===== " represents a triple bond "—C≡C—".

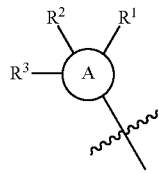 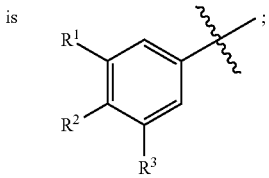

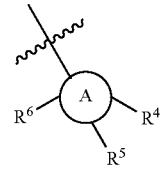 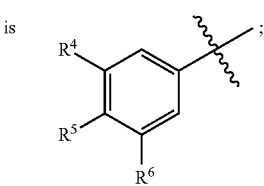

$R^1$ is H, halogen, —$OC_{1-6}$ alkyl or $C_{1-6}$ alkyl;
$R^2$ is H, halogen, —$OC_{1-6}$ alkyl or $C_{1-6}$ alkyl;
$R^3$ is H, halogen, —$OC_{1-6}$ alkyl or $C_{1-6}$ alkyl;
$R^4$ is H, halogen, —$OC_{1-6}$ alkyl or $C_{1-6}$ alkyl;
$R^5$ is H, halogen, —$OC_{1-6}$ alkyl or $C_{1-6}$ alkyl;
$R^6$ is H, halogen, —$OC_{1-6}$ alkyl or $C_{1-6}$ alkyl;
$R^7$H, halogen, —$OC_{1-6}$ alkyl or $C_{1-6}$ alkyl;
$R^8$ is halogen, —$OC_{1-6}$ alkyl, $C_{1-6}$ alkyl, CN, $C(O)R^{11}$, $NR^{12}R^{13}$ or hydroxyl;
$L^1$ is $CH_2$;
$R^{11}$ is H or $C_{1-3}$ alkyl;
a is 0 or 1;
$R^{12}$ is H or $C_{1-3}$ alkyl; and
$R^{13}$ is H or $C_{1-3}$ alkyl.

In another aspect, the invention provides a compound having Formula I wherein
" ===== " represents a triple bond "—C≡C—".

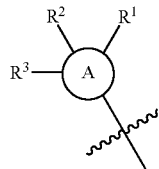 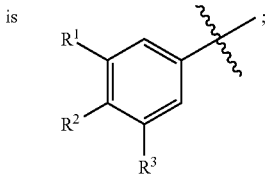

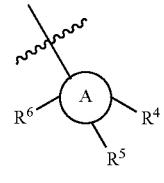 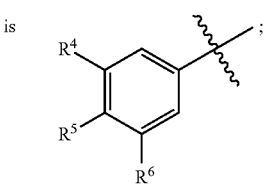

$R^1$ is H, fluoro, methyl, methoxy or chloro;
$R^2$ is H, fluoro, methyl, methoxy or chloro;
$R^3$ is H, fluoro, methyl, methoxy or chloro;
$R^4$ is H, methyl;
$R^5$ is H, methyl;
$R^6$ is H, methyl;
$R^7$ is H, chloro, methyl or bromo;
$L^1$ is $CH_2$;
a is 1.

The term "alkyl", as used herein, refers to saturated, monovalent hydrocarbon moieties having linear or branched moieties or combinations thereof and containing 1 to 8 carbon atoms. One methylene (—$CH_2$—) group, of the alkyl can be replaced by oxygen, sulfur, sulfoxide, nitrogen, carbonyl, carboxyl, sulfonyl, or by a divalent $C_{3-8}$ cycloalkyl. Alkyl groups can be substituted by halogen, hydroxyl, cycloalkyl, amino, non-aromatic heterocycles, carboxylic acid, phosphonic acid groups, sulphonic acid groups, phosphoric acid.

The term "cycloalkyl", as used herein, refers to a monovalent or divalent group of 3 to 8 carbon atoms, derived from a saturated cyclic hydrocarbon. Cycloalkyl groups can be monocyclic or polycyclic. Cycloalkyl can be substituted by $C_{1-8}$ alkyl groups or halogens.

The term "cycloalkenyl", as used herein, refers to a monovalent or divalent group of 3 to 8 carbon atoms, derived from a saturated cycloalkyl having one double bond. Cycloalkenyl groups can be monocyclic or polycyclic. Cycloalkenyl groups can be substituted by $C_{1-8}$ alkyl groups or halogens.

The term "halogen", as used herein, refers to an atom of chlorine, bromine, fluorine, iodine.

The term "alkenyl", as used herein, refers to a monovalent or divalent hydrocarbon radical having 2 to 6 carbon atoms, derived from a saturated alkyl, having at least one double bond. $C_{2-6}$ alkenyl can be in the E or Z configuration. Alkenyl groups can be substituted by $C_{1-8}$ alkyl.

The term "alkynyl", as used herein, refers to a monovalent or divalent hydrocarbon radical having 2 to 6 carbon atoms, derived from a saturated alkyl, having at least one triple bond.

The term "heterocycle" as used herein, refers to a 3 to 10 membered ring, which can be aromatic or non-aromatic, saturated or non-saturated, monocyclic or polycyclic, containing at least one heteroatom selected form O or N or S or combinations of at least two thereof, interrupting the carbocyclic ring structure. The heterocyclic ring can be interrupted by a C=O; the S heteroatom can be oxidized. Heterocycles can be monocyclic or polycyclic. Heterocyclic ring moieties can be substituted by hydroxyl, $C_{1-8}$ alkyl or halogens.

The term "aryl" as used herein, refers to an organic moiety derived from an aromatic hydrocarbon consisting of a ring containing 6 to 10 carbon atoms by removal of one hydrogen. Aryl can be monocyclic or polycyclic. Aryl can be substituted by halogen atoms, $—OC_{1-8}$ alkyl, $C_{1-8}$ alkyl, CN, C(O)H, C(O)($C_{1-8}$ alkyl), $NH_2$, NH($C_{1-8}$ alkyl), N($C_{1-8}$ alkyl) ($C_{1-8}$ alkyl) or hydroxyl. Usually aryl is phenyl. Preferred substitution site on aryl are meta and para positions.

The group of formula "—$CR^{14}$=$CR^{15}$—", as used herein, represents an alkenyl moiety.

The group of formula "—C≡C—", as used herein, represents an alkynyl moiety.

The term "hydroxyl" as used herein, represents a group of formula "—OH".

The term "carbonyl" as used herein, represents a group of formula "—C(O)".

The term "carboxyl" as used herein, represents a group of formula "—C(O)O—".

The term "sulfonyl" as used herein, represents a group of formula "—$SO_2$".

The term "sulfate" as used herein, represents a group of formula "—O—S(O)$_2$—O—."

The term "carboxylic acid" as used herein, represents a group of formula "—C(O)OH".

The term "sulfoxide" as used herein, represents a group of formula "—S=O".

The term "phosphonic acid" as used herein, represents a group of formula "—P(O)(OH)$_2$".

The term "phosphoric acid" as used herein, represents a group of formula "—(O)P(O)(OH)$_2$".

The term "sulphonic acid" as used herein, represents a group of formula "—S(O)$_2$OH".

The formula "H", as used herein, represents a hydrogen atom. The formula "O", as used herein, represents an oxygen atom.

The formula "N", as used herein, represents a nitrogen atom.

The formula "S", as used herein, represents a sulfur atom.

Some compounds of the invention are:
1-{4-[3-(3-chlorophenyl)-4-(3,4-dimethylphenyl)but-1-yn-1-yl]benzyl}azetidine-3-carboxylic acid;
1-{4-[3-(3-Chloro-phenyl)-4-(3,4-dimethyl-phenyl)-but-1-ynyl]-3-methyl-benzyl}-azetidine-3-carboxylic acid;
1-{4-[4-(3,4-dimethylphenyl)-3-(3-methoxyphenyl)but-1-yn-1-yl]benzyl}azetidine-3-carboxylic acid;
1-{4-[3-(4-chlorophenyl)-4-(3,4-dimethylphenyl)but-1-yn-1-yl]benzyl}azetidine-3-carboxylic acid;
1-{4-[4-(3,4-dimethylphenyl)-3-(3-methylphenyl)but-1-yn-1-yl]benzyl}azetidine-3-carboxylic acid;
1-{4-[4-(3,4-Dichloro-phenyl)-3-(3-fluoro-phenyl)-but-1-ynyl]-benzyl}-azetidine-3-carboxylic acid;
1-[4-(3,4-diphenylbut-1-yn-1-yl)benzyl]azetidine-3-carboxylic acid;
1-{4-[(1E)-4-(3,4-dimethylphenyl)-3-(3-fluorophenyl)but-1-en-1-yl]benzyl}azetidine-3-carboxylic acid.

Some compounds of Formula I and some of their intermediates have at least one stereogenic center in their structure. This stereogenic center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like (Handbook of Pharmaceutical Salts, P. Heinrich Stahal & Camille G. Wermuth (Eds), Verlag Helvetica Chemica Acta-Zürich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the sphingosine-1-phosphate receptors.

In another embodiment, there are provided pharmaceutical compositions including at least one compound of the invention in a pharmaceutically acceptable carrier.

In a further embodiment of the invention, there are provided methods for treating disorders associated with modulation of sphingosine-1-phosphate receptors. Such methods can be performed, for example, by administering to a subject in need thereof a pharmaceutical composition containing a therapeutically effective amount of at least one compound of the invention.

These compounds are useful for the treatment of mammals, including humans, with a range of conditions and diseases that are alleviated by S1P modulation.

Therapeutic utilities of S1P modulators are ocular diseases, such as but not limited to: Ocular Diseases: wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis;

Systemic vascular barrier related diseases: various inflammatory diseases, including acute lung injury, its prevention, sepsis, tumor metastasis, atherosclerosis, pulmonary edemas, and ventilation-induced lung injury;

Autoimmune diseases and immnuosuppression: rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermititis, and organ transplantation;

Allergies and other inflammatory diseases: urticaria, bronchial asthma, and other airway inflammations including pulmonary emphysema and chronic obstructive pulmonary diseases;

Cardiac functions: bradycardia, congestional heart failure, cardiac arrhythmia, prevention and treatment of atherosclerosis, and ischemia/reperfusion injury;

Wound Healing: scar-free healing of wounds from cosmetic skin surgery, ocular surgery, GI surgery, general surgery, oral injuries, various mechanical, heat and burn injuries, prevention and treatment of photoaging and skin aging, and prevention of radiation-induced injuries;

Bone formation: treatment of osteoporosis and various bone fractures including hip and ankles;

Anti-nociceptive activity: visceral pain, pain associated with diabetic neuropathy, rheumatoid arthritis, chronic knee and joint pain, tendonitis, osteoarthritis, neuropathic pains;

Anti-fibrosis: ocular, cardiac, hepatic and pulmonary fibrosis, proliferative vitreoretinopathy, cicatricial pemphigoid, surgically induced fibrosis in cornea, conjunctiva and tenon;

Pains and anti-inflammation: acute pain, flare-up of chronic pain, musculo-skeletal pains, visceral pain, pain associated with diabetic neuropathy, rheumatoid arthritis, chronic knee and joint pain, tendonitis, osteoarthritis, bursitis, neuropathic pains;

CNS neuronal injuries: Alzheimer's disease, age-related neuronal injuries;

Organ transplants: renal, corneal, cardiac and adipose tissue transplants.

In still another embodiment of the invention, there are provided methods for treating disorders associated with modulation of sphingosine-1-phosphate receptors. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or a pharmaceutically acceptable salt thereof, for the manufacture of a medicament for the treatment of Ocular Diseases: wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis;

Systemic vascular barrier related diseases: various inflammatory diseases, including acute lung injury, its prevention, sepsis, tumor metastasis, atherosclerosis, pulmonary edemas, and ventilation-induced lung injury;

Autoimmune diseases and immnuosuppression: rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermititis, and organ transplantation;

Allergies and other inflammatory diseases: urticaria, bronchial asthma, and other airway inflammations including pulmonary emphysema and chronic obstructive pulmonary diseases;

Cardiac functions: bradycardia, congestional heart failure, cardiac arrhythmia, prevention and treatment of atherosclerosis, and ischemia/reperfusion injury;

Wound Healing: scar-free healing of wounds from cosmetic skin surgery, ocular surgery, GI surgery, general surgery, oral injuries, various mechanical, heat and burn injuries, prevention and treatment of photoaging and skin aging, and prevention of radiation-induced injuries;

Bone formation: treatment of osteoporosis and various bone fractures including hip and ankles;

Anti-nociceptive activity: visceral pain, pain associated with diabetic neuropathy, rheumatoid arthritis, chronic knee and joint pain, tendonitis, osteoarthritis, neuropathic pains;

Anti-fibrosis: ocular, cardiac, hepatic and pulmonary fibrosis, proliferative vitreoretinopathy, cicatricial pemphigoid, surgically induced fibrosis in cornea, conjunctiva and tenon;

Pains and anti-inflammation: acute pain, flare-up of chronic pain, musculo-skeletal pains, visceral pain, pain associated with diabetic neuropathy, rheumatoid arthritis, chronic knee and joint pain, tendonitis, osteoarthritis, bursitis, neuropathic pains;

CNS neuronal injuries: Alzheimer's disease, age-related neuronal injuries;

Organ transplants: renal, corneal, cardiac and adipose tissue transplants.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of sphingosine-1-phosphate receptors. Thus, in further embodiments of the invention, there are provided methods for treating a disorder associated with modulation of sphingosine-1-phosphate receptors. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of formula I according to the invention can be prepared analogously to conventional methods as understood by the person skilled in the art of synthetic organic chemistry. The synthetic schemes set forth below, illustrate how compounds according to the invention can be made.

Those skilled in the art will be able to routinely modify and/or adapt the following scheme to synthesize any compounds of the invention covered by Formula I.

The following abbreviations are used in the general schemes and in the specific examples:

| | |
|---|---|
| THF | tetrahydrofuran |
| MPLC | medium pressure liquid chromatography |
| NMO | 4-Methylmorpholine N-oxide |
| CH$_3$CN | acetonitrile |

-continued

| | |
|---|---|
| CH$_2$Cl$_2$ | dichloromethane |
| TPAP | Tetrapropylammonium perruthenate |
| MeOH | methanol |
| NaCNBH$_3$ | sodium cyanoborohydride |
| CD$_3$OD | deuterated methanol |
| DMSO-d6 | deuterated dimethyl sulfoxide |
| NaOMe | sodium methoxyde |
| EtOH | ethanol |
| NaBH$_4$ | sodium borohydride |
| MgSO$_4$ | magnesium sulfate |
| NH$_4$Cl | ammonium chloride |
| HCl | hydrochloric acid |
| DIBAL-H | Diisobutylaluminium hydride |
| Et$_2$O | ether |
| MeOH | methanol |
| K$_2$CO$_3$ | potassium carbonate |
| DMF | N,N-dimethylformamide |
| Et$_3$N | triethylamine |
| CuI | cooper iodide |
| PdCl$_2$(PPh$_3$)$_2$ | Bis(triphenylphosphine)palladium(II) chloride |
| NaH | sodium hydride |
| EtOAc | ethylacetate |
| AcOH | acetic acid |
| TFA | trifluoroacetic acid |
| NH$_3$ | ammonia |
| CDCl$_3$ | deuterated chloroform |

General Synthetic Methods

Reaction Schemes A, B and C are examples of general methods for obtaining the compounds disclosed herein.

Reaction Scheme A

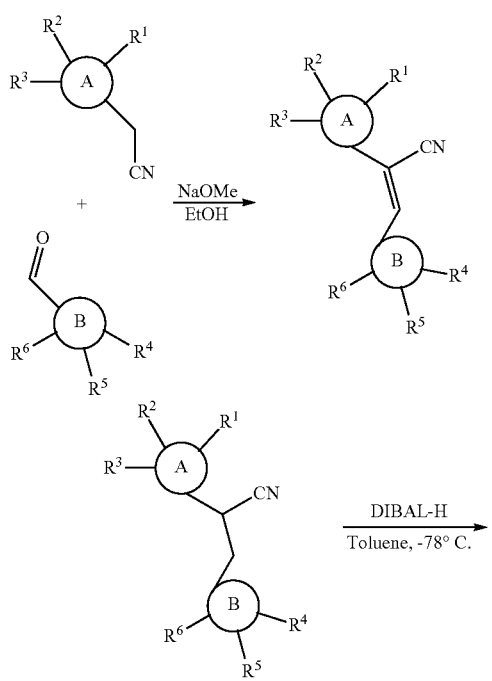

Reaction Scheme B

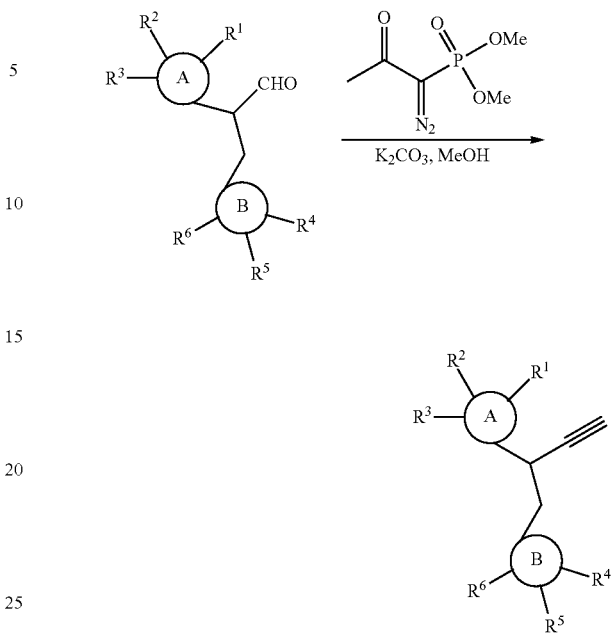

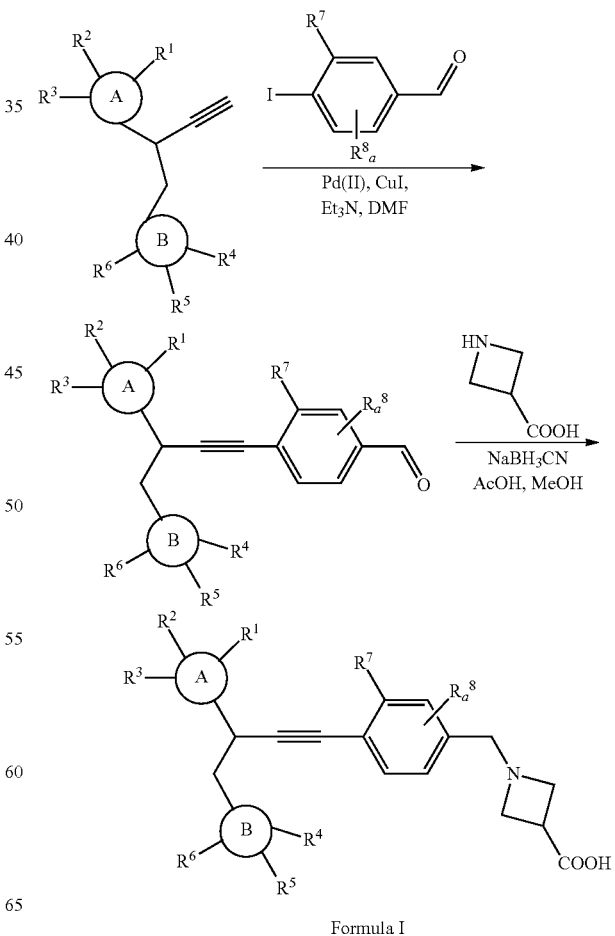

Formula I

Reaction Scheme C

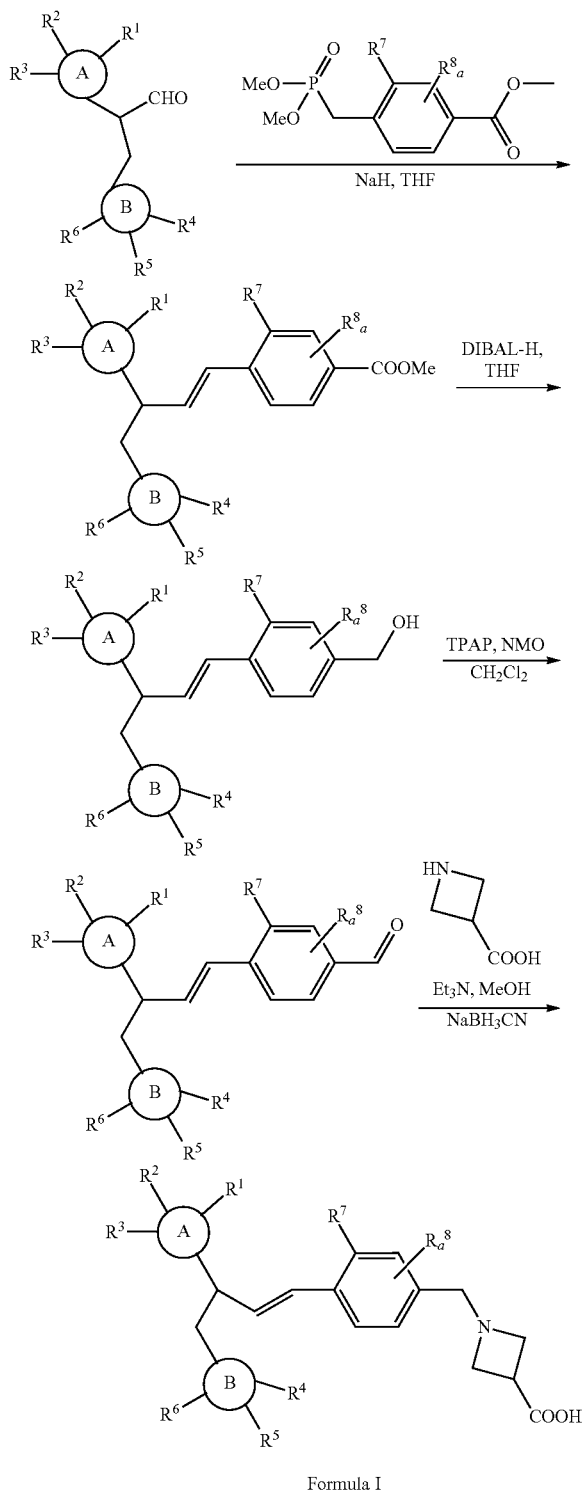

Formula I

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2H$ (or D) in place of protium $^1H$ (or H) or use of $^{13}C$ enriched material in place of $^{12}C$ and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diastereoisomeric isomers, chromatographic separation may be employed.

Compound names were generated with ACD version 8 and intermediates and reagent names used in the examples were generated with software such as Chem Bio Draw Ultra version 12.0 or Auto Nom 2000 from MDL ISIS Draw 2.5 SP1.

In general, characterization of the compounds is performed using NMR spectra, which were recorded on 300 and/or 600 MHz Varian and acquired at room temperature. Chemical shifts are given in ppm referenced either to internal TMS or to the solvent signal.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

Usually the compounds of the invention were purified by column chromatography (Auto-column) on an Teledyne-ISCO CombiFlash with a silica column, unless noted otherwise.

EXAMPLE 1

Intermediate 1

(2E)-2-(3-chlorophenyl)-3-(3,4-dimethylphenyl)acrylonitrile

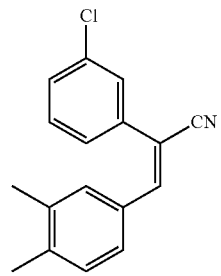 [SMILES: Cc1ccc(/C=C(/C#N)c2cccc(Cl)c2)cc1C]

To a solution of 3,4-dimethylbenzaldehyde (CAS 68844-97-3) (5.0 g, 37.3 mmol) and 3-chloro benzeneacetonitrile (CAS 1529-41-5) (5.63 g, 37.3 mmol) in absolute EtOH 27 mL (0.7 mL/mmol), was added NaOMe (0.1 equiv) portionwise, and stirred at room temperature for 2 h. Then the reaction mixture was cooled to 0° C. and filtered. The precipitate was washed with cold EtOH, and gave Intermediate 1 as a white solid (9.8 g, 98%).

$^1$H NMR (300 MHz, CDCl$_3$) δ: 7.54-7.64 (m, 3H), 7.43-7.49 (m, 1H), 7.39 (s, 1H), 7.24-7.32 (m, 2H), 7.11-7.19 (m, 1H), 2.24 (s, 6H).

EXAMPLE 2

Intermediate 2

2-(3-chlorophenyl)-3-(3,4-dimethylphenyl)propanenitrile

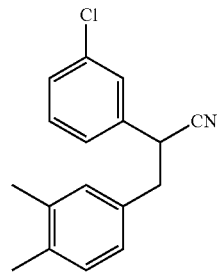 [SMILES: Cc1ccc(CC(C#N)c2cccc(Cl)c2)cc1C]

NaBH$_4$ (2.8 g, 73.4 mmol) was added slowly to a solution of Intermediate 1 (9.8 g, 36.7 mmol) in EtOH (100 mL) under argon. The mixture was stirred at 70° C. for 16 h. The solution was cooled to room temperature and quenched with water. The reaction mixture was diluted with 100 mL water and acidified with 6M HCl (aq.). After extraction with ether (3×100 mL), the combined organic layers were washed with water and brine, dried over MgSO$_4$, filtered and concentrated and gave Intermediate 2 as a white solid (9 g, 91%).

$^1$H NMR (300 MHz, CDCl$_3$) δ: 7.25-7.34 (m, 16H), 7.24-7.35 (m, 3H), 7.13-7.20 (m, 5H), 7.07 (d, J=7.6 Hz, 2H), 6.84-6.94 (m, 2H), 3.95 (dd, J=8.2, 6.4 Hz, 1H), 3.05-3.11 (m, 2H), 2.24 (d, J=2.1 Hz, 6H).

EXAMPLE 3

Intermediate 3

4-[2-(3-chlorophenyl)but-3-yn-1-yl]-1,2-dimethylbenzene

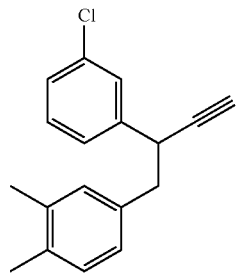 [SMILES: C#CC(Cc1ccc(C)c(C)c1)c1cccc(Cl)c1]

DIBAL-H (1.5 M in toluene, 7 mL, 10.5 mmol) was added dropwise to a solution of Intermediate 2 (2.36 g, 8.78 mmol) in Toluene (36 mL) at −78° C. under argon. The mixture was stirred at −78° C. to −20° C. for 3 h and then quenched by slow addition of saturated NH$_4$Cl solution (2 mL) followed by Celite (2 g) at −20° C. The mixture was diluted with Et$_2$O (50 mL), warmed slowly to room temperature, and stirred till all aluminum precipitated. The solid was filtered and washed with ether (3×50 mL), and the combined organic layers were dried over MgSO$_4$, filtered, concentrated and gave 2-(3-chlorophenyl)-3-(3,4-dimethylphenyl)propanal (2.1 g, 88%).

To a solution of 2-(3-chlorophenyl)-3-(3,4-dimethylphenyl)propanal (1.4 g, 5.1 mmol) in MeOH (30 ml) was added dimethyl (1-diazo-2-oxopropyl)phosphonate (CAS 90965-06-3) at 0° C. followed by K$_2$CO$_3$ (1.4 g, 10.2 mmol). The reaction mixture was stirred at room temperature for 16 hours. The reaction mixture was quenched with water and extracted with CH$_2$Cl$_2$ (3×50 mL), the combined organic layers were dried over MgSO$_4$, filtered and concentrated. The crude product was purified on a column (MPLC) using hexane:ethyl acetate and gave Intermediate 3 (450 mg).

$^1$H NMR (300 MHz, CDCl$_3$) δ 7.4 (s, 1H), 7.3 (m, 3H), 7.1 (d, 1H), 6.9 (m, 2H), 3.85 (m, 1H), 3.0 (m, 2H), 2.35 (s, 1H), 2.25 (s, 6H).

EXAMPLE 4

Intermediate 4

4-[3-(3-chlorophenyl)-4-(3,4-dimethylphenyl)but-1-yn-1-yl]benzaldehyde

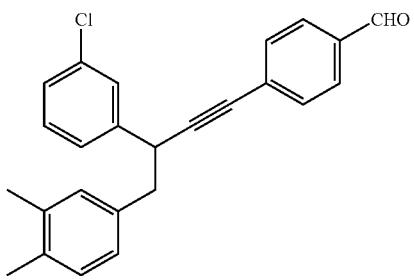 [SMILES: Cc1ccc(CC(C#Cc2ccc(C=O)cc2)c2cccc(Cl)c2)cc1C]

To a solution of Intermediate 3 (445 mg, 1.63 mmol) in anhydrous DMF (10 mL) were added 4-iodobenzaldehyde (417 mg, 1.8 mmol) followed by Et$_3$N (0.68 mL, 4.89 mmol) and CuI (62 mg, 0.326 mmol). The reaction mixture was bubbled with argon, followed by the addition of PdCl$_2$(PPh$_3$)$_2$ (114 mg, 0.163 mmol) under argon. The reaction solution was stirred at room temperature for 16 h. The reaction mixture was quenched with water and extracted with EtOAc (3×50 mL), the combined organic layers were dried over MgSO$_4$, filtered and concentrated. The crude product was purified on a column (MPLC) using hexane:ethyl acetate and gave Intermediate 4 (309 mg).

$^1$NMR (300 MHz, CDCl$_3$) δ 9.99 (s, 1H), 7.78-7.85 (m, 2H), 7.52 (d, J=8.2 Hz, 2H), 7.16-7.29 (m, 3H), 6.85-7.08 (m, 4H), 4.04 (t, J=7.2 Hz, 1H), 3.04 (d, J=7.3 Hz, 2H), 2.24 (d, 6H).

EXAMPLE 5

Intermediate 5

3-(3,4-dimethylphenyl)-2-(3-fluorophenyl)propanal

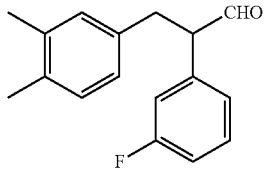 [SMILES: Cc1ccc(CC(C=O)c2cccc(F)c2)cc1C]

To a solution of 3,4-dimethylbenzaldehyde (CAS 68844-97-3) (4.0 g, 29.6 mmol) and 3-fluoro-benzeneacetonitrile (CAS 501-00-8) (4.35 g, 29.6 mmol) in absolute EtOH, 30 mL, was added NaOMe (0.1 equiv), then the reaction mixture was stirred at room temperature for 2 h. The reaction mixture was cooled to 0° C. and filtered. The precipitate was washed with cold EtOH and gave (2E)-3-(3,4-dimethylphenyl)-2-(3-fluorophenyl)acrylonitrile as a white solid (6.20 g, 78%). NaBH$_4$ (1.8 g, 47 mmol) was added slowly to a solution of (2E)-3-(3,4-dimethylphenyl)-2-(3-fluorophenyl)acrylonitrile (6.17 g, 23.5 mmol) in EtOH (100 mL) under argon. The mixture was stirred at 70° C. for 16 h. The solution was cooled to room temperature and quenched with water. The reaction mixture was diluted with 100 mL water and acidified with 6M HCl (aq.). After extraction with ether (3×100 mL), the combined organic layers were washed with water and brine, dried over MgSO$_4$, filtered and concentrated and gave 3-(3,4-dimethylphenyl)-2-(3-fluorophenyl)propanenitrile as a white solid (6 g, 96%). DIBAL-H (1.0 M in toluene, 14 mL, 14 mmol) was added dropwise to a solution of 3-(3,4-dimethylphenyl)-2-(3-fluorophenyl)propanenitrile (2.93 g, 11.72 mmol) in Toluene (40 mL) at −78° C. under argon. The mixture was stirred at −78° C. to −20° C. for 3 h and then quenched by slow addition of saturated NH$_4$Cl solution (2 mL) followed by Celite (2 g) at −20° C. The mixture was diluted with Et$_2$O (50 mL), warmed slowly to room temperature, and stirred till all aluminum precipitated. The solid was filtered and washed with ether (3×50 mL), the combined organic layers were dried over MgSO$_4$, filtered, concentrated and gave Intermediate 5 (2.34 g, 74%).

$^1$H NMR (CDCl$_3$, 300 MHz) δ: 9.72 (d, J=1.5 Hz, 1H), 9.68-9.75 (m, 1H), 7.22-7.36 (m, 1H), 6.83-7.03 (m, 3H), 6.78 (d, J=7.6 Hz, 1H), 3.76-3.87 (m, 1H), 3.38 (dd, J=14.1, 7.0 Hz, 1H), 2.90 (dd, J=14.1, 7.9 Hz, 1H), 2.18 (d, 6H).

EXAMPLE 6

Intermediate 6

{4-[(1E)-4-(3,4-dimethylphenyl)-3-(3-fluorophenyl) but-1-en-1-yl]phenyl}methanol

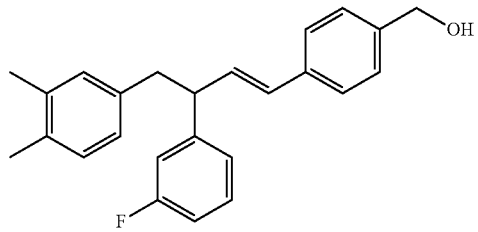 [SMILES: Cc1ccc(CC(/C=C/c2ccc(CO)cc2)c2cccc(F)c2)cc1C]

A solution of methyl 4-[(dimethoxyphosphoryl)methyl]benzoate (CAS 78022-19-2) (2.61 g, 9.14 mmol) in THF 10 (mL) was added to a suspension of NaH (366 mg) in THF (20 mL) at 0° C. and the mixture was stirred at 0° C. for 20 minutes. After 20 minutes a solution of Intermediate 5 (1.8 g, 7.03 mmol) in THF (10 mL) was added to the reaction mixture at 0° C. and stirred at 0° C. for another 2 h. The reaction mixture was quenched with saturated NH$_4$Cl and extracted with ether (3×100 mL), the combined organic layers were dried over MgSO$_4$, filtered, concentrated and gave methyl 4-[(1E)-4-(3,4-dimethylphenyl)-3-(3-fluorophenyl)but-1-en-1-yl]benzoate (2.7 g).

DIBAL-H (1.5 M in toluene, 14 mL, 20.85 mmol) was added dropwise to a solution of 4-[(1E)-4-(3,4-dimethylphenyl)-3-(3-fluorophenyl)but-1-en-1-yl]benzoate (2.7 g, 6.95 mmol) in THF (60 mL) at −78° C. under argon. The mixture was stirred at −78° C. to room temperature for 3 h. The mixture was cooled to −20° C. and then quenched by slow addition of saturated NH$_4$Cl solution (4 mL) followed by Celite (4 g) at −20° C. The mixture was diluted with Et$_2$O (50 mL), warmed slowly to room temperature, and stirred till all aluminum precipitated. The solid was filtered and washed with ether (3×50 mL), and the combined organic layers were dried over MgSO$_4$, filtered, concentrated and gave Intermediate 6 (1.3 g).

$^1$H NMR (CDCl$_3$, 300 MHz) δ: 7.19-7.33 (m, 6H), 6.75-7.01 (m, 5H), 6.23-6.42 (m, 2H), 4.65 (s, 2H), 3.71 (q, J=7.2 Hz, 1H), 3.02 (dd, J=7.5, 3.1 Hz, 2H), 2.19 (d, J=2.9 Hz, 6H).

EXAMPLE 7

Intermediate 7

4-[(1E)-4-(3,4-dimethylphenyl)-3-(3-fluorophenyl) but-1-en-1-yl]benzaldehyde

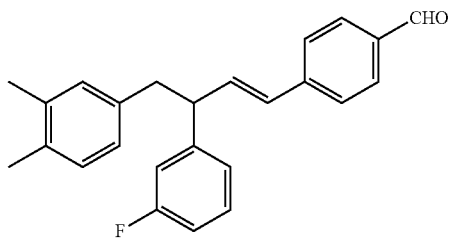 [SMILES: Cc1ccc(CC(/C=C/c2ccc(C=O)cc2)c2cccc(F)c2)cc1C]

To a solution of Intermediate 6 (1.3 g, 3.6 mmol) in anhydrous CH$_2$Cl$_2$ (20 mL), CH$_3$CN (2 mL), were added molecular sieves (500 mg), NMO (845 mg, 7.2 mmol) and TPAP (50 mg) at room temperature. The reaction mixture was stirred at room temperature for 2 h and then passed through a small pad of silicagel column chromatography and eluted in 50% EtOAc in hexane and afforded Intermediate 7 (1.07 g).

¹H NMR (CDCl₃, 300 MHz) δ: 9.95 (s, 1H), 7.79 (d, J=8.2 Hz, 2H), 7.43 (d, J=8.2 Hz, 2H), 6.76-7.03 (m, 7H), 6.24-6.59 (m, 2H), 3.63-3.79 (m, 1H), 3.05 (d, J=7.3 Hz, 2H), 2.19 (d, J=3.2 Hz, 6H).

EXAMPLE 8

Compound 1

1-{4-[3-(3-chlorophenyl)-4-(3,4-dimethylphenyl)but-1-yn-1 yl]benzyl}azetidine-3-carboxylic acid

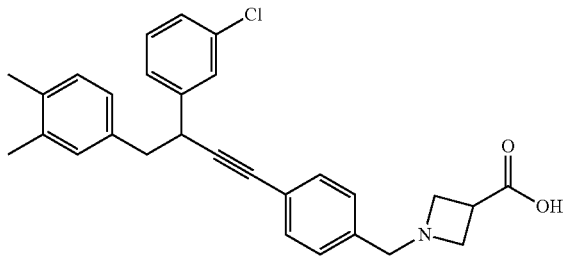 [SMILES: Cc1ccc(CC(C#Cc2ccc(CN3CC(C(=O)O)C3)cc2)c2cccc(Cl)c2)cc1C]

Azetidine-3-carboxylic acid (CAS 36476-78-5) (17 mg, 0.17 mmol) was added to a solution of Intermediate 4 (43 mg, 0.113 mmol) in MeOH (8 mL) followed by AcOH (2 drops) at room temperature. The reaction mixture was stirred at room temperature for 20 minutes then NaCNBH₃ (7 mg, 0.113 mmol) was added to the reaction mixture in 2 mL MeOH. The reaction mixture was stirred at room temperature for 2 h. The reaction mixture was then quenched with water (1 mL) and silica gel was added, concentrated to dryness, then purified on a column (MPLC) using CH₂Cl₂:MeOH and gave Compound 1 (30 mg).

¹NMR (300 MHz, CDCl₃) δ 7.31-7.48 (m, 4H), 7.20-7.31 (m, 3H), 6.80-7.06 (m, 4H), 4.27 (s, 2H), 4.08-4.12 (m, 5H), 3.37 (t, J=8.4 Hz, 1H), 3.01 (dd, J=7.2, 5.1 Hz, 2H), 2.20 (d, J=4.1 Hz, 6H).

Compounds 2 through 8 were prepared in a similar manner to the procedure described in Example 1 for Compound 1. The starting materials and the results are tabulated below in Table 1.

TABLE 1

| Comp. number | IUPAC name | Starting material | ¹NMR (Solvent; δ ppm) |
|---|---|---|---|
| 2 | 1-{4-[3-(3-Chloro-phenyl)-4-(3,4-dimethyl-phenyl)-but-1-ynyl]-3-methyl-benzyl}-azetidine-3-carboxylic acid | Intermediate 3 Benzaldehyde, 4-iodo-3-methyl- (CAS 1160924-07-1) | ¹H-NMR (300 MHz, CD₃OD) δ 7.392-7.218 (7 H, m), 7.003 (1 H, d, J = 7.5 Hz), 6.947 (1 H, s), 6.898 (1 H, d, J = 7.5 Hz), 4.203 (1 H, t, J = 8.1 Hz), 3.841 (2 H, s), 3.721 (2 H, t), 3.591 (2 H, t), 3.233 (1 H, t), 3.007-3.191 (2 H, m), 2.321 (3 H, s), 2.211 (3 H, s), 2.194 (3 H, s). |
| 3 | 1-{4-[4-(3,4-dimethylphenyl)-3-(3-methoxyphenyl)but-1-yn-1-yl]benzyl}azetidine-3-carboxylic acid | 3,4-dimethylbenzaldehyde (CAS 68844-97-3) 3-methoxybenyl)acetonitrile (CAS 19924-43-7) | ¹H NMR (300 MHz, CD₃OD) δ: 7.35-7.44 (m, 4 H), 7.17-7.26 (m, 1 H), 6.75-7.02 (m, 6 H), 4.29 (s, 2 H), 4.16-4.02 (m, 5 H), 3.75 (s, 3 H), 3.35-3.39 (m, 1 H), 2.91-3.07 (m, 2 H), 2.20 (d, J = 3.8 Hz, 6 H) |

TABLE 1-continued

| Comp. number | IUPAC name | Starting material | ¹NMR (Solvent; δ ppm) |
|---|---|---|---|
| 4 | 1-{4-[3-(4-chlorophenyl)-4-(3,4-dimethylphenyl)but-1-yn-1-yl]benzyl}azetidine-3-carboxylic acid | 3,4-dimethylbenzaldehyde (CAS 68844-97-3) Benzene acetonitrile, 4-chloro- (CAS 140-53-4) | ¹H NMR (300 MHz, CD$_3$OD) δ: 7.40 (d, J = 2.9 Hz, 4 H), 7.30 (d, J = 1.8 Hz, 4 H), 6.81-7.01 (m, 3 H), 4.25 (s, 2 H), 4.02-4.15 (m, 5 H), 3.33-3.43 (m, 1 H), 2.96-3.03 (m, 2 H), 2.19 (d, 6 H) |
| 5 | 1-{4-[4-(3,4-Dichloro-phenyl)-3-(3-fluoro-phenyl)-but-1-ynyl]-benzyl}-azetidine-3-carboxylic acid | Benzene acetonitrile, 3-fluoro- (CAS 501-00-8) Benzaldehyde, 3,4-dichloro- (CAS 6287-38-3) | ¹H-NMR (300 MHz, CD$_3$OD) δ: 7.251-7.411 (7 H, m), 7.003-7.210 (3 H, m), 6.981 (1 H, t), 4.211 (1 H, t, J = 7.8 Hz, 3.047-3.067, 3.841 (2 H, s), 3.721 (2 H, t), 3.591 (2 H, t), 3.233 (1 H, t), 3.007-3.191 (2 H, m). |
| 6 | 1-{4-[(1E)-4-(3,4-dimethylphenyl)-3-(3-fluorophenyl)but-1-en-1-yl]benzyl}azetidine-3-carboxylic acid | Intermediate 7 | ¹H NMR (300 MHz, CD$_3$OD) δ: 7.38-7.21 (m, 5 H), 6.74-7.05 (m, 6 H), 6.40-6.54 (m, 1 H), 6.23-6.34 (m, 1 H), 4.26 (s, 2 H), 4.21-4.04 (m, 4 H), 3.72 (q, J = 7.6 Hz, 1 H), 3.33-3.42 (m, 1 H), 2.89-3.06 (m, 2 H), 2.14 (s, 6 H) |
| 7 | 1-{4-[4-(3,4-dimethylphenyl)-3-(3-methylphenyl)but-1-yn-1-yl]benzyl}azetidine-3-carboxylic acid | 3,4-dimethylbenzaldehyde (CAS 68844-97-3) Benzeneacetonitrile, 3-methyl- (CAS 2947-60-6) | ¹H NMR (300 MHz, CD$_3$OD) δ 7.32-7.43 (m, 4 H), 7.08-7.21 (m, 3 H), 7.03 (d, J = 7.0 Hz, 1 H), 6.91-6.99 (m, 2 H), 6.83-6.90 (m, 1 H), 4.26 (s, 2 H), 4.11 (d, J = 8.5 Hz, 4 H), 4.00 (dd, J = 8.4, 6.3 Hz, 1 H), 3.33-3.40 (m, 1 H), 2.85-3.03 (m, 2 H), 2.29 (s, 3 H), 2.18 (d, 6 H) |

TABLE 1-continued

| Comp. number | IUPAC name | Starting material | ¹NMR (Solvent; δ ppm) |
|---|---|---|---|
| 8 | 1-[4-(3,4-diphenylbut-1-yn-1-yl)benzyl]azetidine-3-carboxylic acid | Benzene acetonitrile (CAS 140-29-4) Benzaldehyde (CAS 100-52-7) | ¹H NMR (300 MHz, CD₃OD) δ: 7.27-7.45 (m, 8 H), 7.13-7.26 (m, 6 H), 4.27 (s, 2 H), 4.05-4.18 (m, 5 H), 3.33-3.42 (m, 1 H), 2.98-3.17 (m, 2 H) |

Biological Data

Compounds were synthesized and tested for S1P1 activity using the GTP γ$^{35}$S binding assay. These compounds may be assessed for their ability to activate or block activation of the human S1P1 receptor in cells stably expressing the S1P1 receptor.

GTP γ$^{35}$S binding was measured in the medium containing (mM) HEPES 25, pH 7.4, MgCl$_2$ 10, NaCl 100, dithiothreitol 0.5, digitonin 0.003%, 0.2 nM GTP γ$^{35}$S, and 5 μg membrane protein in a volume of 150 μl. Test compounds were included in the concentration range from 0.08 to 5,000 nM unless indicated otherwise. Membranes were incubated with 100 μM 5'-adenylylimmidodiphosphate for 30 min, and subsequently with 10 μM GDP for 10 min on ice. Drug solutions and membrane were mixed, and then reactions were initiated by adding GTP γ$^{35}$S and continued for 30 min at 25° C. Reaction mixtures were filtered over Whatman GF/B filters under vacuum, and washed three times with 3 mL of ice-cold buffer (HEPES 25, pH7.4, MgCl$_2$ 10 and NaCl 100). Filters were dried and mixed with scintillant, and counted for $^{35}$S activity using a β-counter. Agonist-induced GTP γ$^{35}$S binding was obtained by subtracting that in the absence of agonist. Binding data were analyzed using a non-linear regression method. In case of antagonist assay, the reaction mixture contained 10 nM S1P in the presence of test antagonist at concentrations ranging from 0.08 to 5000 nM.

Table 1 shows activity potency: S1P1 receptor from GTP γ$^{35}$S: nM, (EC$_{50}$).

Activity potency: S1P1 receptor from GTP γ$^{35}$S: nM, (EC$_{50}$),

TABLE 1

| IUPAC name | S1P1 EC$_{50}$ (nM) |
|---|---|
| 1-{4-[4-(3,4-Dichloro-phenyl)-3-(3-fluoro-phenyl)-but-1-ynyl]-benzyl}-azetidine-3-carboxylic acid | 310 |
| 1-{4-[3-(3-Chloro-phenyl)-4-(3,4-dimethyl-phenyl)-but-1-ynyl]-3-methyl-benzyl}-azetidine-3-carboxylic acid | 607 |
| 1-{4-[4-(3,4-dimethylphenyl)-3-(3-methoxyphenyl)but-1-yn-1-yl]benzyl}azetidine-3-carboxylic acid | 42.3 |
| 1-{4-[3-(4-chlorophenyl)-4-(3,4-dimethylphenyl)but-1-yn-1-yl]benzyl}azetidine-3-carboxylic acid | 128 |
| 1-{4-[3-(3-chlorophenyl)-4-(3,4-dimethylphenyl)but-1-yn-1-yl]benzyl}azetidine-3-carboxylic acid | 16 |
| 1-{4-[(1E)-4-(3,4-dimethylphenyl)-3-(3-fluorophenyl)but-1-en-1-yl]benzyl}azetidine-3-carboxylic acid | 58.7 |
| 1-{4-[4-(3,4-dimethylphenyl)-3-(3-methylphenyl)but-1-yn-1-yl]benzyl}azetidine-3-carboxylic acid | 91.9 |

What is claimed is:

1. A compound having Formula I, its enantiomers, diastereoisomers, hydrates, solvates, crystal forms and individual isomers, tautomers or a pharmaceutically acceptable salt thereof,

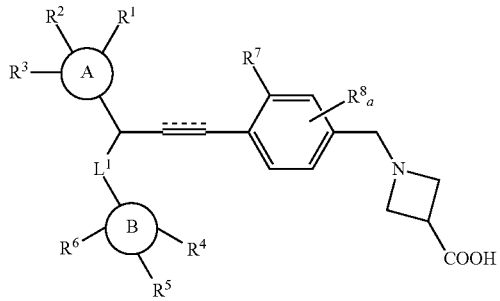

Formula I wherein:
"$=====$" represents a double bond "—CR$^{14}$=CR$^{15}$—" or a triple bond "—C≡C—";

A is C$_{6-10}$ aryl, heterocycle, C$_{3-8}$ cycloalkyl or C$_{3-8}$ cycloalkenyl;

B is C$_{6-10}$ aryl, heterocycle, C$_{3-8}$ cycloalkyl or C$_{3-8}$ cycloalkenyl;

R$^1$ is H, halogen, —OC$_{1-8}$ alkyl, C$_{1-8}$ alkyl, CN, C(O)R$^{11}$, NR$^{12}$R$^{13}$ or hydroxyl;

R$^2$ is H, halogen, —OC$_{1-8}$ alkyl, C$_{1-8}$alkyl, CN, C(O)R$^{11}$, NR$^{12}$R$^{13}$ or hydroxyl;

R$^3$ is H, halogen, —OC$_{1-8}$ alkyl, C$_{1-8}$ alkyl, CN, C(O)R$^{11}$, NR$^{12}$R$^{13}$ or hydroxyl;

R$^4$ is H, halogen, —OC$_{1-8}$ alkyl, C$_{1-8}$ alkyl, CN, C(O)R$^{11}$, NR$^{12}$R$^{13}$ or hydroxyl;

$R^5$ is H, halogen, —$OC_{1-8}$ alkyl, $O_{1-8}$ alkyl, CN, $C(O)R^{11}$, $NR^{12}R^{13}$ or hydroxyl;

$R^6$ is H, halogen, —$OC_{1-8}$ alkyl, $O_{1-8}$ alkyl, CN, $C(O)R^{11}$, $NR^{12}R^{13}$ or hydroxyl;

$R^7$ is H, halogen, —$OC_{1-8}$ alkyl, $C_{1-8}$ alkyl, CN, $C(O)R^{11}$, $C_{6-10}$ aryl, heterocycle, $C_{3-8}$ cycloakyl, $C_{3-8}$ cycloalkenyl, $NR^{12}R^{13}$ or hydroxyl;

$R^8$ is the same or independently halogen, —$OC_{1-8}$ alkyl, $C_{1-8}$ alkyl, CN, $C(O)R^{11}$, $NR^{12}R^{13}$ or hydroxyl;

$L^1$ is O, S, NH or $CH_2$;

$R^{11}$ is H or $O_{1-8}$ alkyl;

a is 0, 1, 2 or 3;

$R^{12}$ is H or $O_{1-8}$ alkyl;

$R^{13}$ is H or $O_{1-8}$ alkyl;

$R^{14}$ is H or $O_{1-8}$ alkyl; and $R^{15}$ is H or $O_{1-8}$ alkyl.

2. A compound according to claim 1 wherein:
" ===== " represents a double bond "—$CR^{14}$=$CR^{15}$—".

3. A compound according to claim 1 wherein:
" ===== " represents a triple bond "—C≡C—".

4. A compound according to claim 1 wherein:
" ===== " is $CH_2$.

5. A compound according to claim 1 wherein:
$L^1$ is O, S or NH.

6. A compound according to claim 1 wherein:

$R^1$ is H, halogen, —$OC_{1-6}$ alkyl or $C_{1-6}$ alkyl;
$R^2$ is H, halogen, —$CO_{1-6}$ alkyl or $O_{1-6}$ alkyl;
$R^3$ is H, halogen, —$OC_{1-6}$ alkyl or $O_{1-6}$ alkyl;
$R^4$ is H, halogen, —$OC_{1-6}$ alkyl or $O_{1-6}$ alkyl;
$R^5$ is H, halogen, —$OC_{1-6}$ alkyl or $O_{1-6}$ alkyl;
$R^6$ is H, halogen, —$_{1-6}$ alkyl or $O_{1-6}$ alkyl;
$R^7$ is H, halogen, —$OC_{1-6}$ alkyl or $O_{1-6}$ alkyl;
$R^8$ is halogen, —$OC_{1-6}$ alkyl, $C_{1-6}$ alkyl, CN, $C(O)R^{11}$, $NR^{12}R^{13}$ or hydroxyl;
$L^1$ is $CH_2$;
$R^{11}$ is H or $O_{1-3}$ alkyl;
a is 0 or 1;
$R^{12}$ is H or $O_{1-3}$ alkyl;
$R^{13}$ is H or $O_{1-3}$ alkyl;
$R^{14}$ is H or $O_{1-3}$ alkyl; and
$R^{15}$ is H or $O_{1-3}$ alkyl.

8. A compound according to claim 1 wherein:
" ===== " represents a triple bond "—C≡C—".

$R^1$ is H, halogen, —$OC_{1-6}$ alkyl or $O_{1-6}$ alkyl;
$R^2$ is H, halogen, —$OC_{1-6}$ alkyl or $O_{1-6}$ alkyl;
$R^3$ is H, halogen, —$OC_{1-6}$ alkyl or $O_{1-6}$ alkyl;
$R^4$ is H, halogen, —$OC_{1-6}$ alkyl or $O_{1-6}$ alkyl;
$R^5$ is H, halogen, —$OC_{1-6}$ alkyl or $O_{1-6}$ alkyl;
$R^6$ is H, halogen, —$OC_{1-6}$ alkyl or $O_{1-6}$ alkyl;
$R^7$ is H, halogen, —$OC_{1-6}$ alkyl or $O_{1-6}$ alkyl;
$R^8$ is halogen, —$OC_{1-6}$ alkyl, $C_{1-6}$ alkyl, CN, $C(O)R^{11}$, $NR^{12}R^{13}$ or hydroxyl;
$L^1$ is $CH_2$;
$R^{11}$ is H or $O_{1-3}$ alkyl;
a is 0 or 1;
$R^{12}$ is H or $O_{1-3}$ alkyl; and
$R^{13}$ is H or $O_{1-3}$ alkyl.

9. A compound according to claim 1 selected from:
1-{4-[3-(3-chlorophenyl)-4-(3,4-dimethylphenyl)but-1-yn-1-yl]benzyl}azetidine-3-carboxylic acid;
1-{4-[3-(3-Chloro-phenyl)-4-(3,4-dimethyl-phenyl)-but-1-ynyl]-3-methyl-benzyl}-azetidine-3-carboxylic acid;
1-{4-[4-(3,4-dimethylphenyl)-3-(3-methoxyphenyl)but-1-yn-1-yl]benzyl}azetidine-3-carboxylic acid;
1-{4-[3-(4-chlorophenyl)-4-(3,4-dimethylphenyl)but-1-yn-1-yl]benzyl}azetidine-3-carboxylic acid;
1-{4-[4-(3,4-dimethylphenyl)-3-(3-methylphenyl)but-1-yn-1-yl]benzyl}azetidine-3-carboxylic acid;
1-{4-[4-(3,4-Dichloro-phenyl)-3-(3-fluoro-phenyl)-but-1-ynyl]-benzyl}-azetidine-3-carboxylic acid;
1-[4-(3,4-diphenylbut-1-yn-1-yl)benzyl]azetidine-3-carboxylic acid;
1-{4-[(1E)-4-(3,4-dimethylphenyl)-3-(3-fluorophenyl)but-1-en-1-yl]benzyl}azetidine-3-carboxylic acid.

10. A pharmaceutical composition comprising as active ingredient a therapeutically effective amount of a compound according to claim 1 and a pharmaceutically acceptable adjuvant, diluents or carrier.

11. A pharmaceutical composition according to claim 10 wherein the compound is selected from:
- 1-{4-[3-(3-chlorophenyl)-4-(3,4-dimethylphenyl)but-1-yn-1-yl]benzyl}azetidine-3-carboxylic acid;
- 1-{4-[3-(3-Chloro-phenyl)-4-(3,4-dimethyl-phenyl)-but-1-ynyl]-3-methyl-benzyl}-azetidine-3-carboxylic acid;
- 1-{4-[4-(3,4-dimethylphenyl)-3-(3-methoxyphenyl)but-1-yn-1-yl]benzyl}azetidine-3-carboxylic acid;
- 1-{4-[3-(4-chlorophenyl)-4-(3,4-dimethylphenyl)but-1-yn-1-yl]benzyl}azetidine-3-carboxylic acid;
- 1-{4-[4-(3,4-dimethylphenyl)-3-(3-methylphenyl)but-1-yn-1-yl]benzyl}azetidine-3-carboxylic acid;
- 1-{4-[4-(3,4-Dichloro-phenyl)-3-(3-fluoro-phenyl)-but-1-ynyl]-benzyl}-azetidine-3-carboxylic acid;
- 1-[4-(3,4-diphenylbut-1-yn-1-yl)benzyl]azetidine-3-carboxylic acid;
- 1-{4-[(1E)-4-(3,4-dimethylphenyl)-3-(3-fluorophenyl)but-1-en-1-yl]benzyl}azetidine-3-carboxylic acid.

* * * * *

UNITED STATES PATENT AND TRADEMARK OFFICE
CERTIFICATE OF CORRECTION

PATENT NO. : 8,492,561 B2
APPLICATION NO. : 13/305701
DATED : July 23, 2013
INVENTOR(S) : Santosh C. Sinha et al.

It is certified that error appears in the above-identified patent and that said Letters Patent is hereby corrected as shown below:

In the Specification

In column 1, line 25, delete "Sphingosine-1 phosphate" and insert -- Sphingosine-1-phosphate --, therefor.

In column 2, line 41, delete "cycloakyl," and insert -- cycloalkyl, --, therefor.

In column 6, lines 10-15, delete " 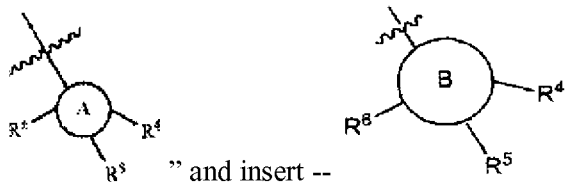 " and insert -- -- , therefor.

In column 6, lines 45-50, delete " 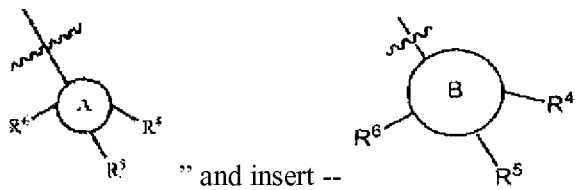 " and insert -- -- , therefor.

In column 6, line 61, delete "1." and insert -- 0. --, therefor.

In column 8, line 49, delete "Stahal" and insert -- Stahl --, therefor.

In column 8, line 50, delete "Chemica" and insert -- Chimica --, therefor.

In column 9, line 28, delete "immnuosuppression:" and insert -- immunosuppression: --, therefor.

In column 9, line 31, delete "antoimmune" and insert -- autoimmune --, therefor.

In column 9, line 33, delete "dermititis," and insert -- dermatitis, --, therefor.

In column 10, line 22, delete "immnuosuppression:" and insert -- immunosuppression: --, therefor.

Signed and Sealed this
Twenty-second Day of October, 2013

Teresa Stanek Rea
*Deputy Director of the United States Patent and Trademark Office*

CERTIFICATE OF CORRECTION (continued)
U.S. Pat. No. 8,492,561 B2

In column 10, lines 25-28, delete "Myasthenia gravis, Psoriasis, ulcerative colitis, antoimmune uveitis, renal ischemia/perfusion injury, contact hypersensitivity, atopic dermititis, and organ transplantation;" and insert the same after "sclerosis," on Col. 10, Line 24 as a continuation of the same Paragraph.

In column 10, lines 25-26, delete "antoimmune" and insert -- autoimmune --, therefor.

In column 10, line 27, delete "dermititis," and insert -- dermatitis, --, therefor.

In column 13, line 9, delete "methoxyde" and insert -- methoxide --, therefor.

In column 13, line 23, delete "cooper" and insert -- copper --, therefor.

In column 16, line 41, delete "diastereoisomeric" and insert -- diastereomeric --, therefor.

In columns 21-22, line 26 (TABLE 1), delete "methoxybenyl" and insert -- methoxybenzyl --, therefor.

In columns 23-24, line 53, delete "(m, 1 H),4.26" and insert -- (m, 1 H), 4.26 --, therefor.

In column 25, line 35, delete "5'-adenylylimmidodiphosphate" and insert -- 5'-adenylylimidodiphosphate --, therefor.

In the Claims

In column 27, line 1, in claim 1, delete "O$_{1-8}$alkyl," and insert -- C$_{1-8}$ alkyl, --, therefor.

In column 27, line 3, in claim 1, delete "O$_{1-8}$alkyl," and insert -- C$_{1-8}$ alkyl, --, therefor.

In column 27, line 6, in claim 1, delete "cycloakyl," and insert -- cycloalkyl, --, therefor.

In column 27, line 12, in claim 1, delete "O$_{1-8}$alkyl;" and insert -- C$_{1-8}$ alkyl; --, therefor.

In column 27, line 14, in claim 1, delete "O$_{1-8}$alkyl;" and insert -- C$_{1-8}$ alkyl; --, therefor.

In column 27, line 15, in claim 1, delete "O$_{1-8}$alkyl;" and insert -- C$_{1-8}$ alkyl; --, therefor.

In column 27, line 16, in claim 1, delete "O$_{1-8}$alkyl;" and insert -- C$_{1-8}$ alkyl; --, therefor.

In column 27, line 17, in claim 1, delete "O$_{1-8}$alkyl." and insert -- C$_{1-8}$ alkyl. --, therefor.

In column 27, line 23, in claim 4, delete " " " and insert -- L$^1$ --, therefor.

In column 27, lines 35-42, in claim 6, delete "  " and insert -- -- , therefor.

In column 27, lines 55-60, in claim 7, delete "  " and insert -- --, therefor.

In column 27, line 65, in claim 7, delete "—CO$_{1-6}$" and insert -- —OC$_{1-6}$ --, therefor.

CERTIFICATE OF CORRECTION (continued)

In column 27, line 65, in claim 7, delete "$O_{1-6}$ alkyl;" and insert -- $C_{1-6}$ alkyl; --, therefor.

In column 27, line 66, in claim 7, delete "$O_{1-6}$ alkyl;" and insert -- $C_{1-6}$ alkyl; --, therefor.

In column 27, line 67, in claim 7, delete "$O_{1-6}$ alkyl;" and insert -- $C_{1-6}$ alkyl; --, therefor.

In column 28, line 1, in claim 7, delete "$O_{1-6}$ alkyl;" and insert -- $C_{1-6}$ alkyl; --, therefor.

In column 28, line 2, in claim 7, delete "—$_{1-6}$" and insert -- —$OC_{1-6}$ --, therefor.

In column 28, line 2, in claim 7, delete "$O_{1-6}$ alkyl;" and insert -- $C_{1-6}$ alkyl; --, therefor.

In column 28, line 3, in claim 7, "$O_{1-6}$ alkyl;" and insert -- $C_{1-6}$ alkyl; --, therefor.

In column 28, line 7, in claim 7, delete "$O_{1-3}$ alkyl;" and insert -- $C_{1-3}$ alkyl; --, therefor.

In column 28, line 9, in claim 7, delete "$O_{1-3}$ alkyl;" and insert -- $C_{1-3}$ alkyl; --, therefor.

In column 28, line 10, in claim 7, delete "$O_{1-3}$ alkyl;" and insert -- $C_{1-3}$ alkyl; --, therefor.

In column 28, line 11, in claim 7, delete "$O_{1-3}$ alkyl;" and insert -- $C_{1-3}$ alkyl; --, therefor.

In column 28, line 12, in claim 7, delete "$O_{1-3}$ alkyl." and insert -- $C_{1-3}$ alkyl. --, therefor.

In column 28, lines 24-30, in claim 8, delete " " and insert -- 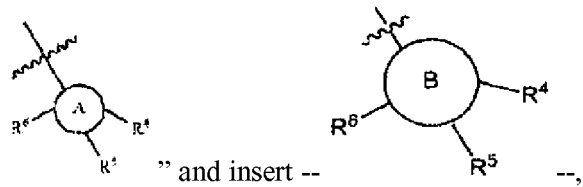 --, therefor.

In column 28, line 33, in claim 8, delete "$O_{1-6}$ alkyl;" and insert -- $C_{1-6}$ alkyl; --, therefor.

In column 28, line 34, in claim 8, delete "$O_{1-6}$ alkyl;" and insert -- $C_{1-6}$ alkyl; --, therefor.

In column 28, line 35, in claim 8, delete "$O_{1-6}$ alkyl;" and insert -- $C_{1-6}$ alkyl; --, therefor.

In column 28, line 36, in claim 8, delete "$O_{1-6}$ alkyl;" and insert -- $C_{1-6}$ alkyl; --, therefor.

In column 28, line 37, in claim 8, delete "$O_{1-6}$ alkyl;" and insert -- $C_{1-6}$ alkyl; --, therefor.

In column 28, line 38, in claim 8, delete "$O_{1-6}$ alkyl;" and insert -- $C_{1-6}$ alkyl; --, therefor.

In column 28, line 39, in claim 8, delete "$O_{1-6}$ alkyl;" and insert -- $C_{1-6}$ alkyl; --, therefor.

In column 28, line 43, in claim 8, delete "$O_{1-3}$ alkyl;" and insert -- $C_{1-3}$ alkyl; --, therefor.

In column 28, line 45, in claim 8, delete "$O_{1-3}$ alkyl;" and insert -- $C_{1-3}$ alkyl; --, therefor.

In column 28, line 46, in claim 8, delete "$O_{1-3}$ alkyl." and insert -- $C_{1-3}$ alkyl. --, therefor.